United States Patent [19]

Ksoll et al.

[11] Patent Number: 5,245,063
[45] Date of Patent: Sep. 14, 1993

[54] PREPARATION OF CARBONYL CHLORIDES

[75] Inventors: Peter Ksoll, Dossenheim; Wolfgang Reuther, Heidelberg; Andreas Hohmann, Ludwigshafen; Peter Wittmer, Neustadt, all of Fed. Rep. of Germany

[73] Assignee: BASF Aktiengesellschaft, Ludwigshafen, Fed. Rep. of Germany

[21] Appl. No.: 757,388

[22] Filed: Sep. 10, 1991

[30] Foreign Application Priority Data

Sep. 11, 1990 [DE] Fed. Rep. of Germany ....... 4028774

[51] Int. Cl.$^5$ .............................................. C07C 51/00
[52] U.S. Cl. .................................... 554/151; 554/154; 554/231; 562/840; 562/846
[58] Field of Search ................ 260/408; 554/151, 154, 554/231; 562/840, 846

[56] References Cited

U.S. PATENT DOCUMENTS 3,547,960 12/1970 Hauser ............................ 260/408
3,857,841 12/1974 Keil ............................ 260/250 R

FOREIGN PATENT DOCUMENTS 2000442 4/1990 Canada .
0367050 5/1990 European Pat. Off. .
0050779 5/1984 Fed. Rep. of Germany .

OTHER PUBLICATIONS

Chemical Abstracts, vol. 114, #11, 1991, pp. 101, 147f.

Primary Examiner—Jose G. Dees
Assistant Examiner—Deborah D. Carr
Attorney, Agent, or Firm—Keil & Weinkauf

[57] ABSTRACT

A process for preparing carbonyl chlorides of the formula I

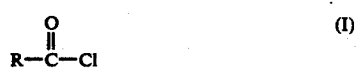

where R is $C_1$–$C_{30}$-alkyl, $C_2$–$C_{30}$-alkenyl or $C_2$–$C_{30}$-alkynyl, from essentially equimolar amounts of a carboxylic acid of the formula II

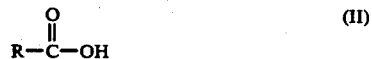

where R has the abovementioned meanings, and phosgene $COCl_2$ (III), in the presence of a catalytic adduct of phosgene and N,N-disubstituted formamide or the hydrochlorides thereof, of the formula IV

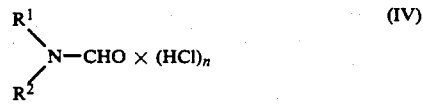

where $R^1$ and $R^2$ are each, independently of one another, $C_1$–$C_3$-alkyl or together are a $C_4$–$C_5$-alkylene chain which may be interrupted by oxygen or by nitrogen which carries $C_1$–$C_3$-alkyl or CHO, and n is 0, 1 or 2, wherein the reaction is carried out with a stationary phase of the catalytic adduct, is described.

5 Claims, No Drawings

PREPARATION OF CARBONYL CHLORIDES

The present invention relates to a novel and improved process for preparing carbonyl chlorides from carboxylic acids and phosgene on a stationary phase composed of a catalytic adduct of phosgene and N,N-disubstituted formamide.

Carbonyl chlorides can be prepared satisfactorily by reacting the corresponding carboxylic acids with phosgene. A catalyst is required for the reaction; for example carboxamides, preferably N-alkylformamides, are used (DE-A-34 39 937).

The size range of the alkyl in the case of N,N-dialkylformamides extends from methyl to radicals with 30 carbon atoms (EP-A-0 050 779, DE-A-29 50 155, DE-A-19 31 074).

The choice of the catalyst system has a crucial influence on the course of the conversion of a carboxylic acid into its chloride with phosgene, and on the working up of the mixture.

A conceivable alternative to the filtration of tar-containing crude products in some cases would be working up of the catalyst-containing product by distillation. However, not only is distillation of the acid chlorides energy- and time-consuming, it also has a number of other disadvantages.

Many long-chain acid chlorides cannot be distilled without partial decomposition. It is also known that the distilled products may be contaminated owing to decomposition of the catalyst in the bottom product during distillation. Large amounts of catalyst residue represent a safety risk during distillation because they may undergo thermal decomposition.

Both filtration and distillation in the working up of contaminated mixtures greatly reduce the activity of the catalyst so that, in most cases, it cannot be used again.

Thus, both distillation and filtration of catalyst-containing carbonyl chlorides represent unsatisfactory methods of working up. Because of the loss of catalyst during working up, the amount of it used must be kept as low as possible.

The catalyst used in DE-A-29 50 155 is diisobutylformamide which is soluble in the reaction mixture throughout the reaction. If it is intended to dispense with final distillation of the acid chloride, the proportion of soluble catalyst must be kept to a minimum for reasons of product purity. Reuse of the catalyst is ruled out with this catalyst system too, because it is discharged with the product.

It is also known that the efficiency of reactions with phosgene increases with the proportion of catalyst. Conversely, small amounts of catalyst mean either that the phosgene passed in is poorly utilized or that it must be passed in for a long time.

DE-A-22 40 883 describes the preparation of carbonyl chlorides with equimolar amounts of carboxylic acid and catalyst. However, in order to remove and recover the large amount of catalyst, it is necessary finally to add a volume of benzene which is 3 to 4 times that of the reaction, followed by distillation of the product solution in benzene.

The use of large amounts of catalyst is also described in JP-10 613/68 for the preparation of linoleoyl chloride using from 10 to 50 mol % of dimethylformamide, but also from 1 to 10 equivalents of dimethylformamide, based on linoleic acid employed. The resulting acid chloride must be distilled and, in some cases, be additionally purified by treatment with active carbon. Reuse of the large amounts of catalyst is not envisaged.

It is a well known problem in the conversion of carboxylic acids into the corresponding chlorides with phosgene that excess phosgene has to be removed from the crude acid chloride.

One prior art possibility is to remove phosgene from phosgene-containing carbonyl chloride by stripping with nitrogen and/or by reducing the pressure slightly, for several hours. This process is time-consuming and considerably reduces the space-time yield.

In DE-A-29 50 155, excess phosgene is distilled over with the first fraction of acid chloride. Besides the reduction in the space-time yield which this also entails, additional apparatus and analyses are needed for this procedure.

DE-A-22 40 883 discloses a working up in which, before the distillation, the diluted reaction solution is briefly washed with ice-water. In view of the sensitivity of carbonyl chlorides to hydrolysis, there are problems with this process on the industrial scale.

It is also necessary in the process disclosed in JP 10613/68 to remove excess phosgene by distillation of the crude acid chloride.

DE-A-38 36 967 discloses a process for preparing higher carbonyl chlorides by 100 % loading of the N,N-dialkylformamide with phosgene. There is a not inconsiderable loss of phosgene in this procedure.

DE-A-40 12 781 discloses a process for preparing carbonyl chlorides either batchwise or continuously in which the catalyst is dispersed by stirring in the acid or acid chloride throughout the reaction. The subsequent phase separation reduces the space-time yield of the process. The long contact time of the products I with the catalyst system at elevated temperature reduces the quality of the product, e.g. in respect of the color. In addition, it is not possible to react long-chain carboxylic acids such as stearic acid below the melting point without solvent.

The dispersion of the catalyst in the acid or acid chloride results in the $CO_2$/HCl off-gas containing $>1.0$ % phosgene, which is not negligible.

It is an object of the present invention to find a process for preparing carbonyl chlorides which remedies the abovementioned disadvantages.

We have found that this object is achieved by a novel and improved process for preparing carbonyl chlorides of the formula I

where R is $C_1$–$C_{30}$-alkyl, $C_2$–$C_{30}$-alkenyl or $C_2$–$C_{30}$-alkynyl, from essentially equimolar amounts of a carboxylic acid of the formula II

where R has the abovementioned meanings, and phosgene $COCl_2$ (III), in the presence of a catalytic adduct of phosgene and N,N-disubstituted formamide of the formula IV

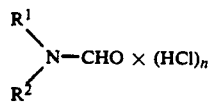

where $R^1$ and $R^2$ are each, independently of one another, $C_1$-$C_3$-alkyl or together are a $C_4$-$C_5$-alkylene chain which may be interrupted by oxygen or by nitrogen which carries $C_1$-$C_3$-alkyl or CHO, and n is 0, 1 or 2, wherein the reaction is carried out with a stationary phase of the catalytic adduct.

The carbonyl chlorides I can be obtained by the following method: The components, the carboxylic acid II and the phosgene III, can be introduced stepwise or continuously at from 20° to 140° C., preferably 45° to 100° C., particularly preferably 30° to 80° C., under from 0.01 to 50 bar, preferably 0.1 to 5 bar, particularly preferably under atmospheric pressure (about 1 bar), into a reactor which is packed with a stationary phase of a catalytic adduct of phosgene and an N,N-disubstituted formamide IV for the reaction.

In the stepwise reaction, it is possible to form the catalytic adduct by passing in phosgene III and then to pass a carboxylic acid II through until the phosgene in the adduct has been consumed, and then to repeat the procedure etc.

In the continuous version, the carboxylic acid II and phosgene III can be passed in essentially equimolar amounts, i.e. in the molar ratio of from 0.8:1 to 1.2:1, preferably 0.95:1 to 1.05:1, particularly preferably 1:1, into the stationary phase of the catalytic adduct.

The rates of flow of the precursors II and III should be such that little or no turbulence occurs in the stationary catalytic adduct phase. Laminar flow in the stationary catalyst phase is particularly preferred.

After the precursors II and III have passed through the stationary catalyst phase, as a rule the carbonyl chloride I automatically separates out as product above the stationary catalyst phase and can be collected in a vessel and then, if necessary, purified by conventional methods such as distillation or crystallization. However, the quality of the product is generally such that purification is unnecessary.

Suitable reactors are all the customary types such as tube reactors, loop reactors and tanks, with the proviso that the thickness of the catalyst layer is such that, when there is laminar flow of phosgene, no dispersion is formed with the acid or the acid chloride, preferably vertical tube reactors into which the precursors are fed from the bottom.

The progress of the reaction can be monitored by physical methods, such as measurement of the density, conductivity and chloride content.

Suitable probes for measuring conductivity are electrodes measuring by induction or directly, preferably the former.

The probes for measuring conductivity are positioned in the reactor, preferably in the catalyst phase.

The conductivities during the reaction were from 10 to 15 mS/cm (millisiemens/centimeter), preferably from 10.5 to 14.5, particularly preferably from 11 to 14 mS/cm.

The ratio of the height to the diameter of the reactor and/or of the stationary catalytic adduct is greater than or equal to 0.2, i.e. 0.2 to 500, preferably greater than or equal to 1, i.e. 1 to 200, particularly preferably 10 to 50.

The stationary catalyst phase, i.e. the catalytic adduct of phosgene and N,N-substituted formamide x(HCl)$_n$ IV with n=0, 1 or 2 may comprise a mixture of the following compounds:

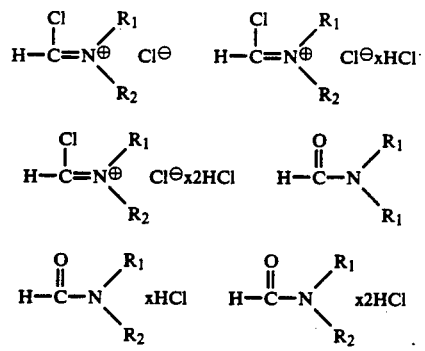

The catalyst loading is from 0.1 to 95 mol %, preferably 10 to 80 mol %, especially 20 to 70 mol %.

The catalyst loading can be determined continuously by measuring the density, the viscosity, the conductivity or the chloride content of the heavier phase in the separator.

Phase separation takes place in the reactor at from 20° to 100° C., preferably 30° to 80° C., especially 40° to 70° C.

The phosgene (III) and the carboxylic acid (II) are used in essentially equimolar amounts.

Since the off-gas from the reaction contains only very small amounts of phosgene (0.0001 to 0.1 %), besides carbon dioxide and hydrogen chloride, no condensation of the phosgene is necessary. The off-gases can be fed to the scrubber immediately. Thus, the off-gas needs to be cooled only enough for maximum condensation of the required product.

It is possible, for improved phase separation or for the reaction of solid acids, to add to the reaction mixture a solvent which is inert under the reaction conditions, such as saturated aliphatic hydrocarbons, ethers, acetonitrile, benzene, toluene or cyclohexane.

A particular advantage of the process is that even solid acids can be reacted without solvent at temperatures below their melting points.

The carbonyl chloride is produced in high yield and high purity. It can often be used further without additional purification. In some cases a single distillation is necessary in order to obtain a product of high purity. The carbonyl chlorides obtained after the reaction contain no phosgene and thus no measures for removing it from the crude acid chloride are necessary.

The process according to the invention for preparing acid chlorides from aliphatic carboxylic acids is especially suitable for monocarboxylic acids, i.e. for preparing compounds of the formula RCOX where R is an aliphatic group and X is chlorine. The aliphatic group can be straight-chain or branched, saturated or olefinically or acetylenically unsaturated. Particularly preferred aliphatic carboxylic acids have from 1 to 30, in particular 1 to 20, carbon atoms.

Suitable N,N-dialkylformamides are dimethyl-, ethylmethyl-, methyl-n-propyl-, methylisopropyl-, diethyl-, ethyl-n-propyl-, ethylisopropyl-, di-n-propyl-, n-propylisopropyl- and diisopropylformamide, preferably dimethyl- and diethylformamide, particularly preferably diethylformamide.

EXAMPLES

Loading of the Catalyst 7 mol (707 g) of diethylformamide are introduced into a 2 L glass tube reactor packed with Raschig rings. The catalytic adduct is formed by passing in phosgene at 60° C. until the conductivity has reached 14 mS/cm, which corresponds to 95 % loading.

EXAMPLE 1

Preparation of Stearoyl Chloride

Molten stearic acid was metered at a rate of 2.3 mol/h into the prepared catalyst at 60° C. At the same time, phosgene was passed in so that the conductivity was from 11 to 14 mS/cm, which corresponded to from 40 to 95% loading.

The stearoyl chloride emerged from the reactor after about 20 min and was cooled to 25° C. and obtained by phase separation in a conventional manner. The yield was 99.7 % with iodine color number 5.

EXAMPLE 2

Preparation of Oleoyl Chloride

Oleic acid was metered at a rate of 1.3 mol/h into the prepared catalyst at 60° C. At the same time, phosgene was passed in so that the conductivity was from 11 to 14 mS/cm, which corresponded to from 40 to 95 % loading.

The oleoyl chloride emerged from the reactor after about 20 min and was cooled to 25° C. and obtained by phase separation in a conventional manner. The yield was 96.0 % with iodine color number 30.

EXAMPLE 3

Preparation of 2 Ethylhexanoyl Chloride

2 Ethylhexanoic acid was metered at a rate of 2.5 mol/h into the prepared catalyst at 60° C. At the same time, phosgene was passed in so that the conductivity was from 11 to 14 mS/cm, which corresponded to from 40 to 95% loading.

The 2-ethylhexanoyl chloride emerged from the reactor after about 20 min and was cooled to 25° C. and obtained by phase separation in a conventional manner. The yield was 97.5 % with iodine color number 26.

We claim:

1. A process for preparing a carbonyl chloride of the formula I

where R is $C_1$–$C_{30}$-alkyl, $C_2$–$C_{30}$-alkenyl or $C_2$–$C_{30}$-alkynyl, from essentially equimolar amounts of a carboxylic acid of the formula II

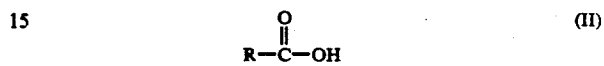

where R has the abovementioned meanings, and phosgene $COCl_2$ (III), in the presence of a catalytic adduct of phosgene and N,N-disubstituted formamide or the hydrochlorides thereof, of the formula IV

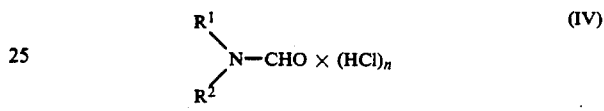

where $R^1$ and $R^2$ are each, independently of one another, $C_1$–$C_3$-alkyl or together are a $C_4$–$C_5$-alkylene chain which may be interrupted by oxygen or by nitrogen which carries $C_1$–$C_3$-alkyl or CHO, and n is 0, 1 or 2, wherein the reaction is carried out with a stationary phase of the catalytic adduct.

2. A process as claimed in claim 1, wherein the reaction is carried out stepwise or continuously, and the formamide (IV) is loaded with from 0.1 to 95 mol % of phosgene.

3. A process as claimed in claim 1, wherein the reaction is carried out stepwise or continuously.

4. A process as claimed in claim 1, wherein the N,N-dialkylformamide is N,N-dimethylformamide, N-methyl-N-ethylformamide or N,N-diethylformamide.

5. A process as claimed in claim 1, wherein the N,N-dialkylformamide is N,N-diethylformamide.

* * * * *